United States Patent [19]

Chockalingam

[11] Patent Number: 5,278,335
[45] Date of Patent: Jan. 11, 1994

[54] PREPARATION OF ARYL-SUBSTITUTED ALIPHATIC CARBOXYLIC ACID ESTERS BY CATALYTIC CARBONYLATION

[75] Inventor: Kannappan Chockalingam, Baton Rouge, La.

[73] Assignee: Ethyl Corporation, Richmond, Va.

[21] Appl. No.: 60,186

[22] Filed: Jun. 11, 1993

[51] Int. Cl.$^5$ ............................................. C07C 69/76
[52] U.S. Cl. ........................................ 560/105; 562/406
[58] Field of Search .......................... 560/105; 562/406

[56] References Cited

U.S. PATENT DOCUMENTS 4,424,394  1/1984  Schneider et al. .................. 560/165
4,439,618  3/1984  Cometti et al. ..................... 560/105

Primary Examiner—Paul J. Killos
Attorney, Agent, or Firm—Richard J. Hammond

[57] ABSTRACT

A new process for preparing alkyl esters of ibuprofen is provided. A 1-halo-1-(4-isobutylphenyl)ethane is reacted with carbon monoxide in the presence of an anhydrous alcohol at a temperature between about 10° C. and about 200° C. An excess of several moles of alcohol is preferred. An acid such as trifluoroacetic acid is also added. As catalyst, a mixture of a copper compound and a palladium or a palladium compound and at least one acid-stable ligand are present.

9 Claims, No Drawings

PREPARATION OF ARYL-SUBSTITUTED ALIPHATIC CARBOXYLIC ACID ESTERS BY CATALYTIC CARBONYLATION

TECHNICAL FIELD

This invention relates to a process for preparing aryl-substituted aliphatic carboxylic acid esters

BACKGROUND OF THE INVENTION

Among the processes known for preparing 2-(4-isobutylphenyl)propionic acid or esters thereof is that of Shimizu et al (U.S. Pat. No. 4,694,100, issued September, 1987), who teach the reaction of p-isobutyl-styrene with carbon monoxide water or alcohol in the presence of a palladium catalyst and a mineral acid, e.g., HCl. This patent also teaches the alternative reaction of p-isobutylstyrene with carbon monoxide and hydrogen in the presence of a metal complex carbonyl catalyst to produce 2-(4-isobutylphenyl)propionaldehyde, which is then oxidized to produce the desired product The preparation of the starting material for this reaction is disclosed as the reaction of isobutylbenzene with acetaldehyde in the presence of sulfuric acid, producing 1,1-bis(4-isobutylphenyl)ethane, which is then catalytically cracked to produce p-isobutylstyrene and isobutyl-benzene.

Another process for preparing ibuprofen is that of European Patent Application 284,310 (Hoechst Celanese, published September, 1988), which teaches that ibuprofen can be prepared by carbonylating 1-(4-isobutylphenyl)ethanol with carbon monoxide in an acidic aqueous medium and in the presence of a palladium compound/phosphine complex and dissociated hydrogen and halide ions, which are preferably derived from a hydrogen halide. This process has the disadvantage of starting with 1-(4-isobutyl-phenyl)ethanol, a compound which is not economical to make by known processes.

Gardano et al. (U.S. Pat. No. 4,536,595, issued August, 1985) teach the preparation of alkaline salts of certain alpha-arylpropionic acids by reaction with carbon monoxide, at substantially ambient temperature and pressure conditions, of the corresponding arylethyl secondary halide in an anhydrous alcoholic solvent in the presence of alkaline hydroxides and, as catalyst, a salt of cobalt hydrocarbonyl.

Alper et al. in *J. Chem. Soc. Chem. Comm.*, 1983, 1270–1271, discloses the alkenes can react with carbon monoxide, water, hydrochloric acid and a mixture of palladium and copper to produce the hydrocarboxylated product, branched chain carboxylic acid. Oxygen is necessary to succeed in the reaction. Subsequently, Alper et al. have disclosed similar catalyst systems, but employing a chiral ligand, as being successful in asymmetric hydrocarboxylation reactions. See Alper et al., PCT Application, WO 91 03,452 and *J. Am. Chem. Soc.*, 112, 2803–2804 (1990).

Japanese Kokiku Patent No. SHO (1981)-35659 disclose an anhydrous method of producing a 2-(4-isobutylphenyl) propion acid ester by treating 2-(4-isobutyl-phenyl) ethanol with carbon monoxide in a solution of an alkanol and a catalyst such as palladium/-bis(triphenylphosphine)dichloro complex. The solution may also contain up to ten percent (10%) of a mineral acid, such as hydrogen chloride.

THE INVENTION

In the following specification, the meaning of the substituent groups is as follows: "alkyl" means straight or branched chain alkyl having 1 to 20 carbon atoms and includes, for example, methyl, ethyl, propyl, isopropyl, butyl, isobutyl, secondary butyl, tertiary butyl, pentyl, isopentyl, neopentyl, hexyl, heptyl, octyl, 2-ethylhexyl, 1,1,3,3-tetramethylbutyl, nonyl, decyl, dodecyl, tetradecyl, hexadecyl, octadecyl and eicosyl and "halo" (or halogen) means fluoro, chloro, bromo and iodo.

In accordance with the present invention, an ibuprofen alkyl ester is prepared by carbonylating a 1-halo-1-(4-iso-butylphenyl)ethane with carbon monoxide in an anhydrous acidic medium containing at least 1 mol of a $C_1$ to about $C_6$ linear or branched aliphatic alcohol per mol of halo compound at a temperature of between about 25° C. and about 200° C. and a carbon monoxide pressure of at least about one atmosphere in the presence of a trihaloacetic acid (trichloroacetic acid or trifluoroacetic acid). The process is carried out in the presence of a palladium compound in which the palladium has a valence of 0-2, a copper compound, the copper compound having a valence of 1 or 2 and at least one acid-stable ligand.

The present invention embraces any racemates and individual optical isomers thereof of the compounds of the following formula (I) having a chiral carbon atom.

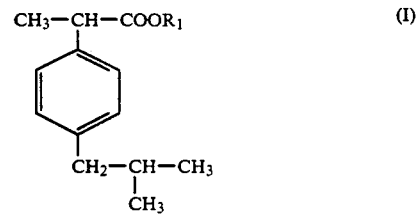

where $R_1$ is alkyl.

The 1-halo-1-(4-isobutylphenyl)ethane which is carbonylated in the practice of this invention is preferably 1-chloro-1-(4-isobutylphenyl)ethane or 1-bromo-1-(4-isobutylphenyl)ethane, which may be synthesized by any known technique.

The carbonylation of 1-halo-1-(4-isobutylphenyl)ethane is conducted at a temperature between about 10° C. and about 200° C., preferably about 50°-150° C., and most preferably about 90°-135° C. Higher temperatures can also be used. It has been found that a small advantage in yield is obtained by gradually increasing the temperature within the preferred ranges during the course of the reaction.

The partial pressure of carbon monoxide in the reaction vessel is at least about 1 atmosphere at ambient temperature (or the temperature at which the vessel is charged). Any higher pressures of carbon monoxide can be used up to the pressure limits of the reaction apparatus. A pressure up to about 4500 psig (about 31 MPa) is convenient in the process. More preferred is a pressure from about 300 to about 3000 psig (about 2 to about 21 MPa) at the reaction temperature, and most preferred is a pressure from about 800 to about 2000 psig (about 5 to about 14 MPa).

The carbonylation is conducted in the presence of at least about one mol of an anhydrous alcohol, preferably $C_1$ to about $C_6$ linear or branched aliphatic alcohol, per mol of 1-halo-1-(4-isobutylphenyl)ethane. However, an excess of the preferred in order to assist in driving the reaction to completion. There is no real upper limit to the amount of added alcohol except that imposed by practicality (e.g. the size of the reaction vessel). An amount up to about 100 mols per mol of 1-halo- 1-(4-isobutylphenyl)ethane is useful in the process Further, controlling the amount of alcohol used in the process of this invention is advantageous in terms of producing the highest yields. Therefore, an amount from about 3 to about 50 mols of alcohol per mol of 1-halo-1-(4-isobutylphenyl)ethane is preferred, and an amount from about 3 to about 24 mols of alcohol per mol of the such compound is most preferred. The product of the reaction is an ester of ibuprofen.

Any alcohol which produces an ester of ibuprofen may be used in the practice of this invention. In a preferred embodiment, the lower aliphatic alcohols, i.e., $C_1$ to $C_6$ linear or branched aliphatic alcohols, are used. Examples of the alcohols to be used in this embodiment include methyl alcohol, ethyl alcohol, n-propyl alcohol, isopropyl alcohol, n-, iso- sec- , and tert-butyl alcohols, the pentyl alcohols, the hexyl alcohols, etc. Methyl alcohol is highly preferred, and ethyl alcohol is most highly preferred. Other alcohols, glycols, or aromatic hydroxy compounds may also be used.

In a preferred embodiment of this invention, the carbonylation reaction is initiated in the presence of a catalytically effective amount of an added perhalogenated acid. Such acids include halo-substituted acetic acids such as trichloroacetic acid or trifluoroacetic acid. Trifluoroacetic acid is preferred. The acid is added in the gas phase or as a liquid phase (in the form of an alcoholic solution). Any acid concentration may be used. However, it is preferred that the acid is used at a solution concentration of up to about 10%; more highly preferred is a solution concentration from about 10% to about 30%. The amount of acid added is such as to provide up to about 40 mols of hydrogen ion per mol of 1-halo-1-(4-isobutylphenyl)ethane; more preferred is an amount to provide up to about 10 mols of hydrogen ion per mol of 1-halo-1-(4-isobutylphenyl)ethane; the most preferred amount provides up to about 4 mols of hydrogen ion per mol of 1-halo-1-(4-isobutylphenyl)ethane. It should be noted, however, that alcoholic materials must be anhydrous to effect improved yields of the ibuprofen ester. Hence, drying of the alcohol solvent/reactant is important for the process of the present invention.

In addition to the perhalogenated acid, the carbonylation process of this invention is conducted in the presence of a reaction-promoting quantity of a) a mixture of a palladium compound in which the palladium is palladium metal or has a valence of 1-2 and a copper compound, the copper having a valence of 1 or 2, and b) at least one acid-stable ligand. Ligands which may be used include monodentate or multidentate electron-donating substances such as those containing elements P, N, O and the like, and those containing multiple bonds such as olefinic compounds. Examples of such acid-stable ligands are trihydrocarbylphosphines, including trialkyl- and triarylphosphines, such as tri-n-butyl-, tricyclohexyl-, and triphenylphosphine; lower alkyl and aryl nitriles, such as benzonitrile and n-propionitrile; ligands containing pielectrons, such as an allyl compound or 1,5-cyclooctadiene; piperidine, piperazine, trichlorostannate(II), and acetylacetonate; and the like.

In one embodiment, the palladium and copper are added as a pre-formed complex of palladium(II) chloride or bromide, copper(II) chloride or bromide and carbon monoxide or any other similar complex. In a preferred embodiment, active catalytic species are formed in situ by the addition to the reaction mixture of the individual components, i.e., a ligand, a copper compound and a palladium compound such as the inorganic salts of copper(II) and palladium(II). These salts include the chlorides, bromides, nitrates, sulfates, or acetates. In the most preferred embodiment, triphenylphosphine, copper(II) chloride and palladium(II) chloride are used and are added individually or together, either simultaneously or sequentially.

The amount of copper compounds and palladium or compounds of palladium preferably employed are such as to provide from about 4 to about 8000 mols of 1-halo-1-(4-isobutylphenyl)ethane per mol of the mixture of copper a palladium; more preferred is an amount to provide from about 10 to about 4000 mols of 1-halo-1-(4-isobutylphenyl)ethane per mol of the copper-palladium mixture; the most preferred amounts provide from about 10 to 2000 mols of 1-halo-1-(4-isoutylphenyl)ethane per mol of the copper compound and palladium or palladium compound mixture. The process of this invention is conducted in the presence of at least one mol of ligand per mol of the mixture of copper and palladium or palladium compound. More preferably about 2 to about 40 mols of ligand per mol of copper and palladium compounds are present, and most preferably about 4 to about 20 mols of ligand per mol of copper and palladium compounds are used. Even more highly preferred is an amount from about 8 to about 12 mols of ligand per mol of copper and palladium compound.

The presence of a solvent is not required in the process of this invention since excess anhydrous alcohol may provide any effects desired from a solvent. However, another solvent may be desirable in some circumstances. Those solvents which can be used include one or more of the following: ketones, for example, acetone, methyl ethyl ketone, diethyl ketone, methyl-n-propyl ketone, acetophenone, and the like; linear, poly and cyclic ethers, for example, diethyl ether, di-n-propyl ether, di-n-butyl ether, ethyl-n-propyl ether, glyme (the dimethyl ether of ethylene glycol), diglyme (the dimethyl ether of diethylene glycol), tetrahydrofuran, dioxane, 1,3-dioxolane, and similar compounds; and aromatic hydrocarbons, for example, toluene, ethyl benzene, alkyl-substituted benzenes such as isobutylbenzene, xylenes, and similar compounds. Alcohols other than the one used to form the desired ibuprofen ester can be used. Alcohols suitable as solvents include for example, methanol, ethanol, 1-propanol, 2-propanol, isomers of butanol, isomers of pentanol, etc. Acids and esters may also be used, such as formic or acetic acid or ethyl acetate, etc. When an ester or an alcohol is used as solvent, the product is the corresponding ester of ibuprofen or a mixture of the esters if mixtures of alcohols or alcohols and acids (or esters) are used.. Most highly preferred are ethers, especially dioxane. When solvents are used, the amount can be up to about 100mL per gram of 1-halo-1-(4-isobutylphenyl)ethane, but the process is most advantageously conducted in the presence of about 1 to 10 mL per gram of 1-halo-1-(4-isobutylphenyl)ethane.

The ester of ibuprofen formed by the process of the present invention is easily converted to the carboxylic acid by conventional methods of hydrolysis.

The following examples are given to illustrate the process of this invention and are not intended as a limitation thereof.

EXAMPLES

Example 1

A mixture of CEBB (0.98 g, 5 mmol), PdCl$_2$ (18 mg, 0.1 mmol), CuCl$_2$ (50 mg, 0.37 mmol), Ph$_3$P (130 mg, 0.5 mmol), trifluoroacetic acid (0.1 mL), and anhydrous methanol (0.7 mL, 17.3 mmol) in 1,4-dioxane (35 mL) was heated at 108°-111° C. under 900 psig of CO.

GC analysis (after 15 hours): PME (91.6%), heavies (3.2%), others (5.2%).

Example 2

A mixture of CEBB (0.98 g, 5 mmol), PdCl$_2$ (25 mg, 0.14 mmol), CuCl$_2$ (50 mg, 0.37 mmol), Ph$_3$P (210 mg, 0.8 mmol), trifluoroacetic acid (0.4 mL), and anhydrous methanol (1 mL, 24.7 mmol) in MEK (35 mL) was heated at 88°-92° C. under 800 psig of CO.

GC analysis (after 28 hours): PME (59.3%), CEBB (18%), MEBB (15.8%), heavies (3.6%), others (2.5%).

Example 3

A mixture of CEBB (0.98 g, 5 mmol), PdCl$_2$ (18 mg, 0.1 mmol), CuCl$_2$ (50 mg, 0.37 mmol), Ph$_3$P (130 mg, 0.5 mmol), trifluoroacetic acid (0.1 mL), and anhydrous isopropanol (1.2 mL, 15.7 mmol) in 1,4-dioxane was heated at 109°-112° C. under 900 psig of CO.

GC analysis (after 10 hours): PIE (86.5%), CEBB (6.5%), heavies (2.9%), others (4.1%).

PME=Methyl 2-(4-isobutylphenyl)propanoate
PIE=Isopropyl 2-(4-isobutylphenyl)propanoate
CEBB=4-(1-chloroethyl)isobutylbenzene
MEBB=4-(1-methoxyethyl)isobutylbenzene It is obvious that many variations may be made in the products and processes set forth above without departing from the spirit and scope of this invention.

I claim:

1. A process for preparing an ester of ibuprofen which comprises carbonylating a 1-halo-1-(4-isobutylphenyl)ethane with carbon monoxide in a neutral or acidic anhydrous medium containing at least about 1 mol of an alcohol per mol of 1-halo-1-(4-isobutylphenyl)ethane at a temperature between about 10° C. and about 200° C. and a carbon monoxide pressure. of at least about one atmosphere in the presence, of catalytically effective amount of a (a) perhaloacetic acid; (b) a mixture of the inorganic salts of copper and palladium metal or the inorganic salts of palladium and (c) at least one acid-stable. ligand.

2. A process of claim 1 wherein the 1-halo-1-(4-isobutylphenyl)ethane is 1-chloro-1-(4-isobutylphenyl)ethane.

3. A process of claim 1 wherein the inorganic salts of palladium is a palladium(II) salt and the inorganic salts of copper is a copper(II) salt.

4. A process of claim 3 wherein the palladium salt is palladium(II) chloride and the copper salt is copper(II) chloride.

5. A process of claim 1 wherein the ligand is a monodentate phosphine ligand.

6. A process of claim 5 wherein the ligand is triphenylphosphine.

7. A process of claim 1 wherein the carbonylation is conducted in the presence of anhydrous methyl alcohol.

8. A process for preparing ibuprofen which comprises carbonylating 1-chloro-1-(4-isobutylphenyl)ethane with carbon monoxide in an anhydrous medium containing dioxane as a solvent and about 3-24 mols of anhydrous methanol per mol of said 1-chloro-1-(4-isobutylphenyl)ethane at a temperature in th of about 50°-150° C. and a carbon monoxide pressure in the range of about 800-1000 psig in the presence of (a) a mixture of a copper(II) compound and a palladium(II) compound and (b) at least one acid-stable monodentate phosphine ligand and in the presence of an amount of trifluoroacetic acid such as to provide an amount up to about 10 mols of hydrogen ions per mol of 1-chloro-1-(4-isobutylphenyl)ethane.

9. A process of claim 8 wherein the copper(II) compound is copper(II) chloride, the palladium(II) compound is palladium(II) chloride and the ligand is triphenylphosphine.

* * * * *

UNITED STATES PATENT AND TRADEMARK OFFICE
CERTIFICATE OF CORRECTION

PATENT NO. : 5,278,335
DATED      : January 11, 1994
INVENTOR(S) : Kannappan Chockalingam It is certified that error appears in the above-indentified patent and that said Letters Patent is hereby corrected as shown below:

Title page, item [22], change "Jun." to --May--.

Signed and Sealed this

Twenty-third Day of August, 1994

Attest:

BRUCE LEHMAN

*Attesting Officer*      *Commissioner of Patents and Trademarks*